(12) United States Patent
Sun et al.

(10) Patent No.: US 7,715,604 B2
(45) Date of Patent: May 11, 2010

(54) SYSTEM AND METHOD FOR AUTOMATICALLY REGISTERING THREE DIMENSIONAL CARDIAC IMAGES WITH ELECTRO-ANATOMICAL CARDIAC MAPPING DATA

(75) Inventors: Yiyong Sun, Lawrenceville, NJ (US);
Fred S. Azar, Princeton, NJ (US);
Chenyang Xu, Allentown, NJ (US);
Frank Sauer, Princeton, NJ (US);
Norbert Rahn, Forchheim (DE)

(73) Assignees: Siemens Medical Solutions USA, Inc., Malvern, PA (US); Siemens Aktiengesellschaft, Munich (DE)

( * ) Notice: Subject to any disclaimer, the term of this patent is extended or adjusted under 35 U.S.C. 154(b) by 882 days.

(21) Appl. No.: 11/330,633

(22) Filed: Jan. 12, 2006

(65) Prior Publication Data
US 2006/0159323 A1 Jul. 20, 2006

Related U.S. Application Data

(60) Provisional application No. 60/644,817, filed on Jan. 18, 2005.

(51) Int. Cl.
*G06K 9/00* (2006.01)
*G06K 9/32* (2006.01)
*A61B 5/05* (2006.01)
(52) U.S. Cl. ................... 382/128; 382/131; 382/294; 600/424
(58) Field of Classification Search ............... 382/128, 382/130–132, 294; 600/424
See application file for complete search history.

(56) References Cited

U.S. PATENT DOCUMENTS

| 5,531,520 | A | * | 7/1996 | Grimson et al. ............. 382/131 |
| 6,556,695 | B1 | * | 4/2003 | Packer et al. ................ 382/128 |
| 6,633,686 | B1 | * | 10/2003 | Bakircioglu et al. ........ 382/294 |
| 6,650,927 | B1 | * | 11/2003 | Keidar ........................ 600/424 |
| 6,735,465 | B2 | * | 5/2004 | Panescu ...................... 600/509 |
| 6,892,091 | B1 | | 5/2005 | Ben-Haim et al. |
| 7,001,383 | B2 | * | 2/2006 | Keidar ........................ 606/41 |
| 7,327,872 | B2 | * | 2/2008 | Vaillant et al. ............. 382/154 |
| 2004/0006268 | A1 | * | 1/2004 | Gilboa et al. ............... 600/424 |
| 2004/0077942 | A1 | * | 4/2004 | Hall et al. ................... 600/428 |
| 2005/0080328 | A1 | * | 4/2005 | Vass et al. ................... 600/407 |
| 2005/0148818 | A1 | * | 7/2005 | Mesallum .................. 600/116 |
| 2005/0171508 | A1 | * | 8/2005 | Gilboa ........................ 604/528 |
| 2006/0229594 | A1 | * | 10/2006 | Francischelli et al. ........ 606/27 |
| 2007/0078325 | A1 | * | 4/2007 | Fuimaono et al. ........... 600/407 |

OTHER PUBLICATIONS

Besl, P.J., et al. (Feb. 1992) "A method for registration of 3-D shapes." IEEE Trans. on Pattern Analysis and Machine Intelligence, vol. 14 No. 2, pp. 239-256.*

(Continued)

*Primary Examiner*—Brian P Werner
*Assistant Examiner*—Barry Drennan (57) ABSTRACT

A system and method for automatically registering a three dimensional (3D) pre-operative image of an anatomical structure with intra-operative electrophysiological (EP) points of a 3D electro-anatomical (EA) image map of the anatomical structure is disclosed. The pre-operative image is displayed in a first supporting view. The intra-operative EA image map is displayed in a second supporting view. An alignment of the pre-operative image with the intra-operative map is performed by identifying at least one corresponding point on each image. The view of the pre-operative image is integrated with the EA map based on the alignment.

18 Claims, 4 Drawing Sheets

OTHER PUBLICATIONS

Fright, W.R., et al. (Sep. 1993) "Registration of 3-D head surfaces using multiple landmarks." IEEE Trans. on Medical Imaging, vol. 12 No. 3, pp. 515-520.*

Sra, J., et al. (Apr. 2003) "Synchronized registration of left atrium for atrial fibrillation ablation." Pacing and Clinical Electrophysiology, vol. 26 Issue 4p2, p. 955, Poster Abstract 108.*

Sun, Y., et al. (Feb. 2005) "Registration of high-resolution 3D atrial images with electroanatomical cardiac mapping: evaluation of registration methodology." Medical Imaging 2005: Visualization, Image-Guided Procedures, and Display, SPIE vol. 5744, pp. 299-307.*

Maurer, C.R., et al. (Feb. 1998) "Registration of head CT images to physical space using multiple geometric features." SPIE Conf. On Image Processing, SPIE vol. 3338, pp. 72-80.*

Dickfeld et al. (Oct. 2004) "Stereotactic magnetic resonance guidance for anatomically targeted ablations of the fossa ovalis and the left atrium." J. Interventional Cardiac Electrophysiology, vol. 11 No. 2, pp. 105-115.*

* cited by examiner

SYSTEM AND METHOD FOR AUTOMATICALLY REGISTERING THREE DIMENSIONAL CARDIAC IMAGES WITH ELECTRO-ANATOMICAL CARDIAC MAPPING DATA

CROSS REFERENCE TO RELATED APPLICATION

This application claims the benefit of U.S. Provisional Application Ser. No. 60/644,817 filed on Jan. 18, 2005, which is incorporated by reference in its entirety.

FIELD OF THE INVENTION

The present invention is directed to a system and method for automatically registering three dimensional cardiac images with electro-anatomical cardiac mapping data, and more particularly, to a system and method for automatically registering pre-operative three dimensional atrial images with intra-operative electro-anatomical cardiac mapping data.

BACKGROUND OF THE INVENTION

Cardiovascular disease is one of the leading causes of death in the United States as well as in many other countries. Cardiovascular disease includes a number of conditions affecting the structures or functions of the heart. Arrhythmias can be an indication of a number of heart problems. An Electrophysiology (EP) test can be performed to record the electrical activity of the heart and to measure the electrical pathways of the heart. An EP test is used to determine the cause of a heart rhythm disturbance and to diagnosis an appropriate course of treatment.

An EP test uses electro-anatomical mapping that traces the movement of electrical signals through the heart. Sensors located at the tip of specially designed catheters acquire data at various points within the heart to pinpoint locations of irregular rhythms or arrhythmias. In some instances, ablation is performed which uses radio frequency signals to kill the cells in the heart muscle that are causing the abnormal rhythm. Fluoroscopic images are used assist the physician in guiding the catheter through the heart. However, fluoroscopic images are two dimensional and do not have good resolution thereby making navigation difficult. There is a need for a system capable of visualizing three dimensional high resolution images which can then be registered with the electro-anatomical mapping data to provide a roadmap for procedures used to identify and treat cardiac arrhythmias.

SUMMARY OF THE INVENTION

The present invention is directed to a system and method for automatically registering a three dimensional (3D) pre-operative image of an anatomical structure with intra-operative electrophysiological (EP) points of a 3D electro-anatomical (EA) image map of the anatomical structure. The pre-operative image is displayed in a first supporting view. The intra-operative EA image map is displayed in a second supporting view. An alignment of the pre-operative image with the intra-operative map is performed by identifying at least one corresponding point on each image. The view of the pre-operative image is integrated with the EA map based on the alignment.

BRIEF DESCRIPTION OF THE DRAWINGS

Preferred embodiments of the present invention will be described below in more detail, wherein like reference numerals indicate like elements, with reference to the accompanying drawings.

DETAILED DESCRIPTION

The present invention is directed to a system and method for automatically registering pre-operative high-resolution three dimensional (3D) cardiac images with corresponding intra-operative electrophysiological (EP) points of 3D electro-anatomical (EA) maps. The 3D images can be obtained using either a Computed Tomography (CT) imaging system or a Magnetic Resonance (MR) imaging system. Registration of left atrial (LA) high-resolution CT and MR images with a cardiac mapping system can provide precise cardiac anatomical information, along with real-time cardiac electrical activation information, catheter tracking and 3D location, and lesion position.

Figure 1:
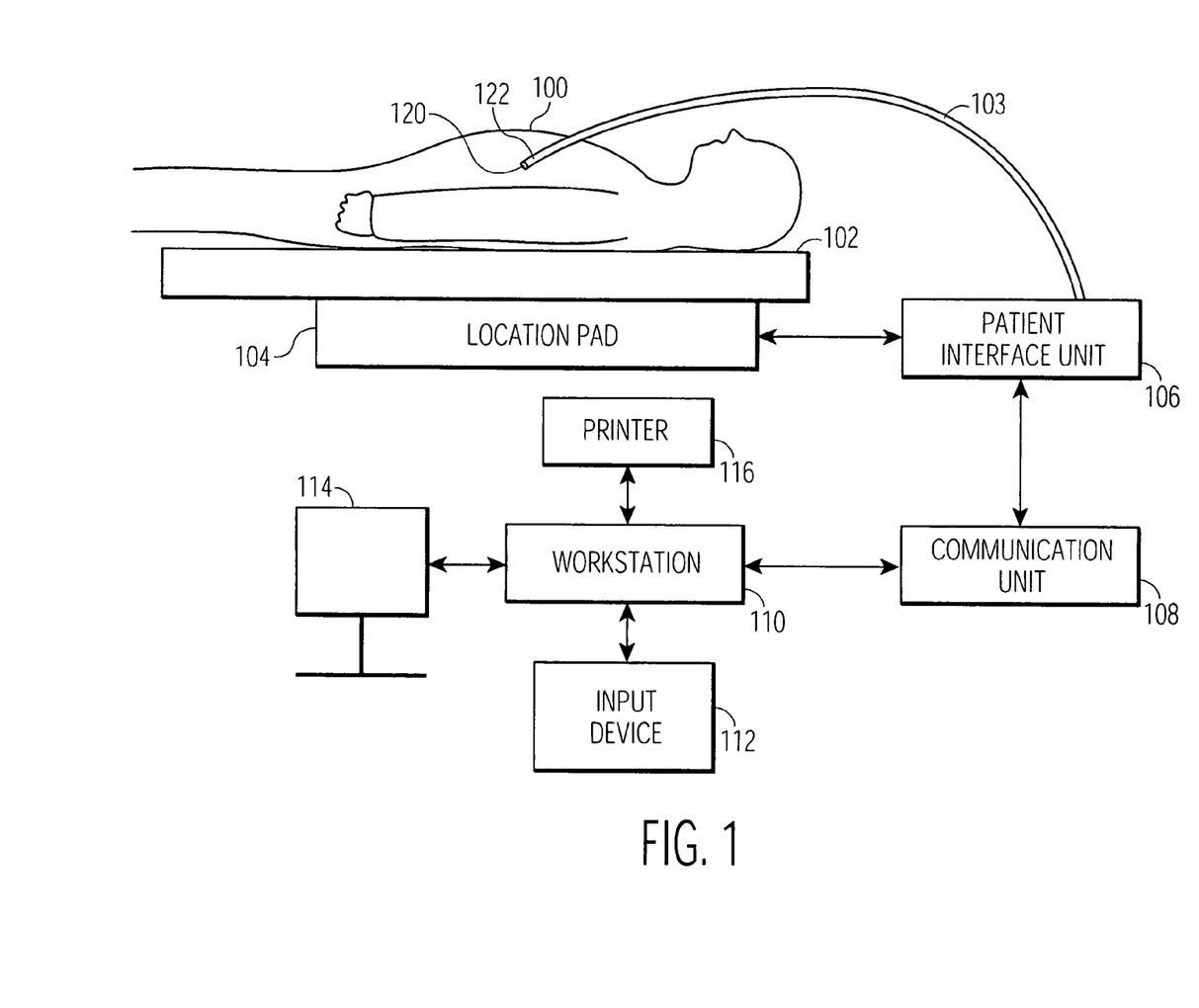
FIG. 1 is a schematic block diagram of a cardiac mapping and navigation system capable of registering three dimensional images with electro-anatomical mapping data in accordance with the present invention.

An exemplary cardiac mapping and navigation system is illustrated in FIG. 1. The cardiac mapping system comprises a miniature passive magnetic field sensor 120 which is located at a tip of a catheter 122 which is inserted in a chamber of a patient's heart. The patient 100 is placed on a patient table 102. A location pad 104 is placed directly under the patient table 102 which is capable of accurately detecting and locating sensor 120. A Patient Interface Unit (PIU) 106 connects the location pad 104 to a communication unit 108. The catheter 122 is also connected to the PIU via cable 103. The PIU 106 also provides cabling connections between the communication unit 108 and all other systems. The communication unit 108 is the processing unit which determines all location and electrocardiogram (ECG) calculations. A workstation 110 connected to the communication unit 108 maintains all of the patient data and cardio maps. In accordance with the present invention, the workstation 110 is also loaded with a set of pre-operative images of the patient as will be described in greater detail hereinafter. The workstation 110 is connected to an input device 112 such as a mouse, keypad or other similar device. The workstation 110 is also connected to a printer 116 for printing out the cardio maps and a monitor 114 which displays the patient data and maps to the physician. The mapping system combines EP information with the 3D anatomy of the heart chambers and yields a 3D map of EA points or an EA map.

The present invention uses an iterative closest point algorithm to automatically register the 3D segmented surface of the left atrium with the patient's corresponding EA map. In accordance with the present invention, the registration of the pre-operative images with the cardio maps is designed to be flexible so that various workflows can be implemented. The present invention allows registration to be computed for each individual chamber of the heart or can support registration of multiple chambers at the same time.

Figure 2:
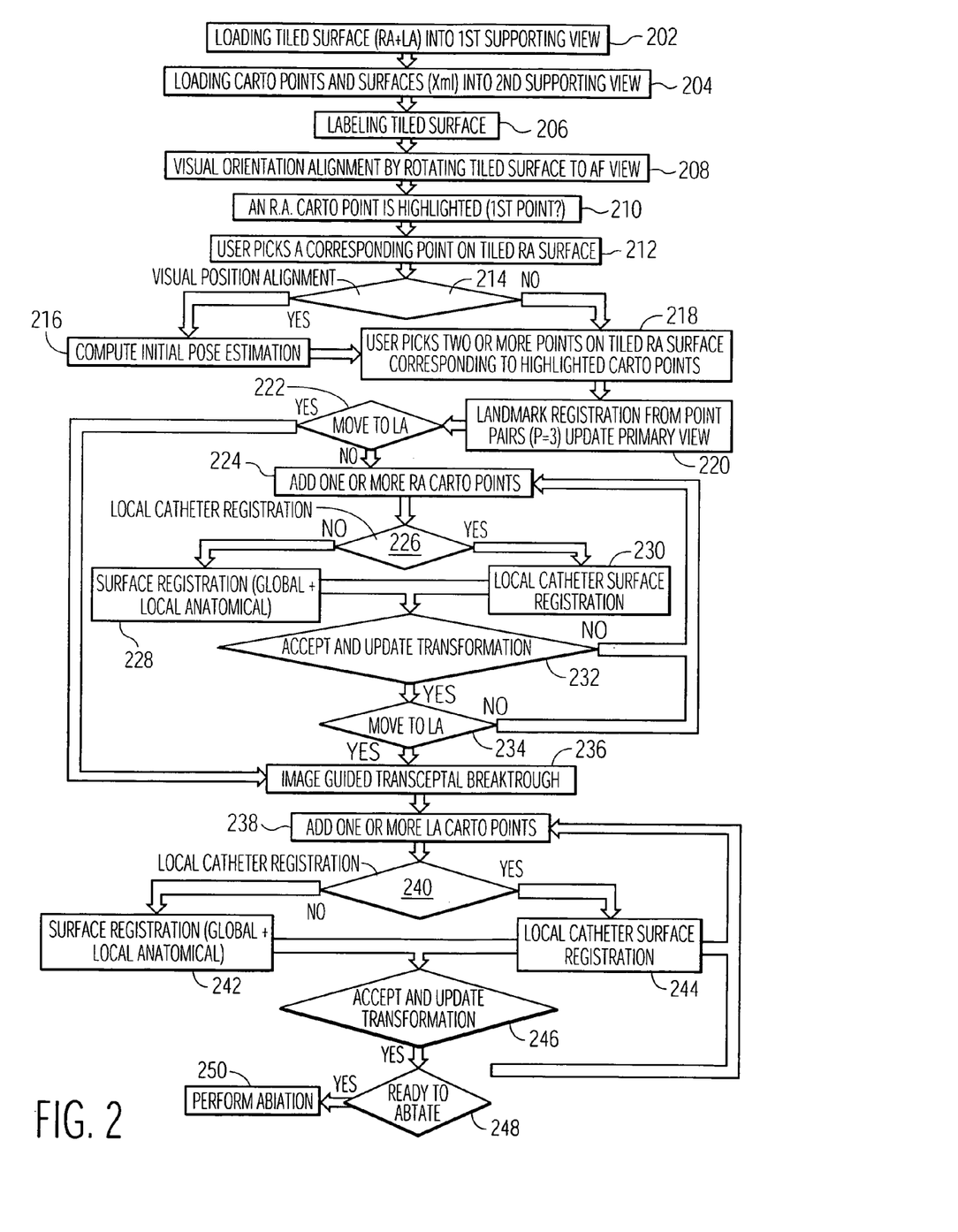
FIG. 2 is a flow chart of a work flow for registering pre-operative 3D atrial images with a cardio map in accordance with the present invention.

FIG. 2 illustrates a flow chart of one such workflow. In this workflow process, the Right Atrium (RA) is first registered using landmark registration to guide the transseptal puncture. Then the RA registration result is used for the initialization of LA surface-based registration. By performing registration of the RA first, less time and calculation is required to register the LA. This is important since the LA is a more vulnerable chamber since it is the primary source of oxygenated blood to the patient. However, registration of other chambers or the heart or parts of the heart such as the aorta may be performed first without departing from the scope or spirit of the present invention. In other instance a limited registration of the LA is performed and then a full registration which also reduces the overall calculations required.

The inputs to the workflow are EA points and a segmented surface that is represented by a dense triangle mesh typically of 20-50 thousand triangles. The output is a rigid transformation matrix that describes the spatial relationship between the EA points and the segmented surface, where the reference coordinate system is of EA points. The rigid transformation matrix contains a 3×3 rotation matrix and a 3D translation vector.

With reference to FIG. 2, a tiled surface of the RA and LA are loaded into the first supporting view (step 202). The EA points and surfaces are loaded into a second supporting view (step 204). Next the tile surface is labeled based upon the type of registration technique used (step 206). Examples of the types of registration techniques which may be used are described in further detail hereinafter. A visual orientation alignment is performed by rotating the tiled surface to an anterior posterior (AP) view (step 208). A RA EA point is acquired (step 210). The user then picks a corresponding point on the tiled RA surface (step 212).

Next a determination is made as to whether the visual alignment will be performed (step 214). If the visual alignment will be performed, the initial pose estimation is computed by visual alignment (step 216). If the visual alignment will not be performed, the user picks two or more points on the tiled RA surface corresponding to the acquired EA points (step 218). Landmark registration is then performed using the point pairs and the view is updated (step 220).

Next a decision is made as to whether to register the LA image with the mapping points (step 222). If more registration data is needed, one or more RA EA points are added (step 224). Next it is determined if the locally optimal registration will be performed (step 226). If the locally optimal registration will be not performed, surface registration is performed (step 228). After the catheter is registered, a determination is made to accept and update the transformation (step 232). If the transformation is not updated, more RA EA points are added and the flow goes back to step 224. If the transformation is accepted, registration of the LA begins (step 234).

Next is the image guided transseptal breakthrough (step 236). One or more LA EA points are added to the image (step 238). Next a determination is made as to whether a locally optimal registration will be performed (step 240). If the locally optimal registration will not be performed, surface registration is performed (step 242). If the catheter is registered (step 244), the transformation is reviewed for acceptance and update (step 246). If the transformation is accepted, the image registration result can be used to aid LA ablation (steps 248, 250). Otherwise further registration is performed.

Figure 3:
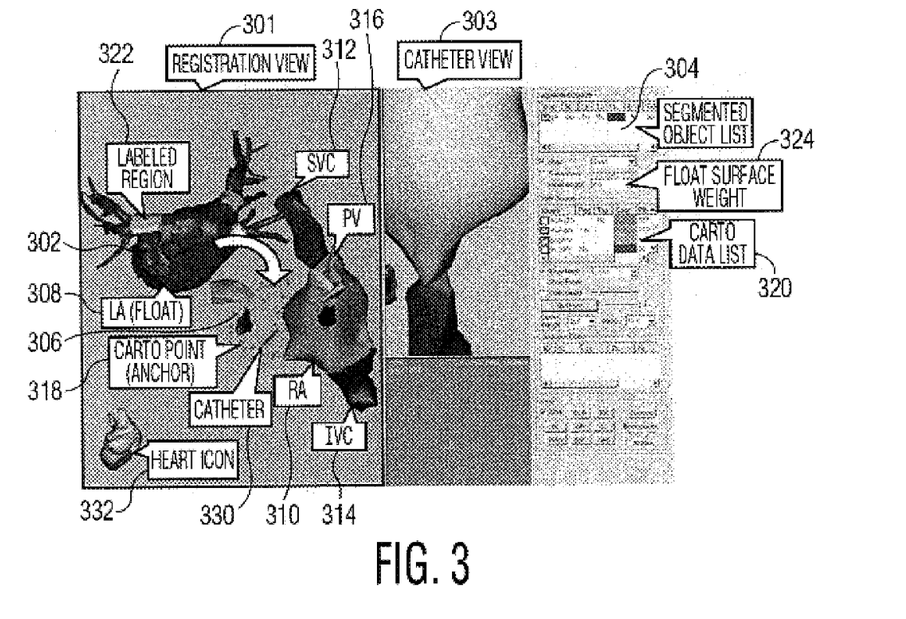
FIG. 3 illustrates an example of a graphical user interface to be used with the system of FIG. 1 and a left atrium prior to registration in accordance with the present invention.
Figure 4:
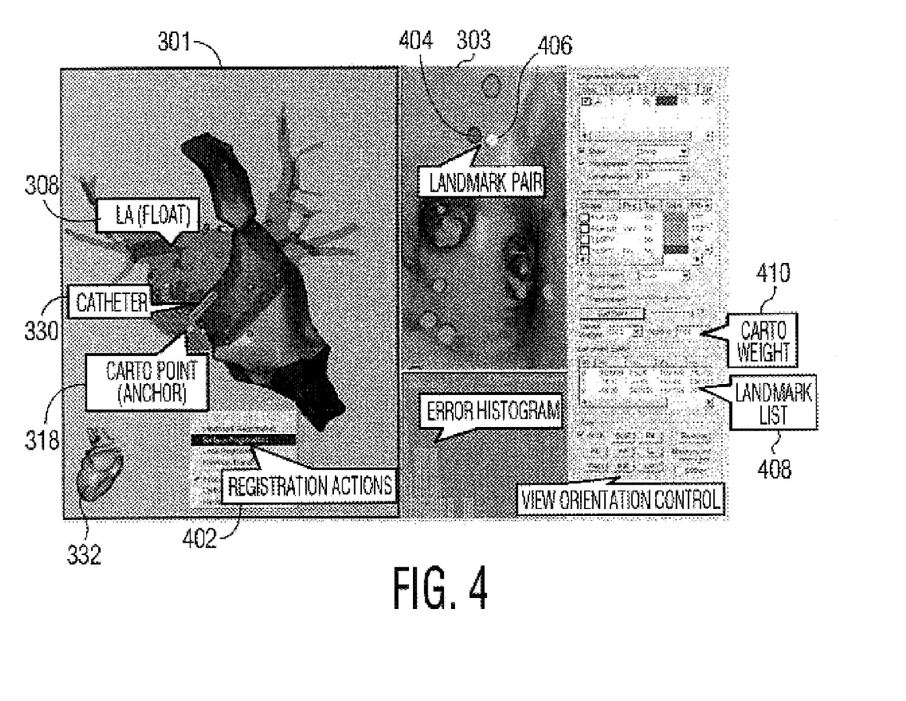
FIG. 4 illustrates an example of the left atrium of FIG. 3 after registration.

FIGS. 3 and 4 illustrate an example of left atrium registration of the anatomical surface and mapping data before and after registration. The segmented surface of the LA 302 is loaded and displayed in the registration view. More than one surface for different chambers can be loaded. The list 304 of segmented objects is displayed in the dialog bar 304. The mapping data 306 is displayed in the registration view. EP data of LA 302, RA 310, Superior Vena Cava (SVC) 312, Inferior Vena Cava (IFC) 314 and Pulmonary Veins (PV) 316 are loaded. Data of each chamber contain the EA points and interpolated surfaces. Only EA points of the LA are shown in the FIGS. 3 and 4. Interpolated surfaces are only used for visualization purposes and not used for registration. The list of EA data is displayed in the dialog bar 320.

The LA segmented surface 308 is considered to be the floating object and will be registered to the EA points of LA that is regarded as anchor or reference 318. Regions 322 on the LA 302 are labeled regions that are assigned with different weights to achieve local anatomy registration. The weight is controlled by a drop down menu on the dialog bar 324. A catheter 330 is shown in the registration view 301. A perspective camera (not shown) is attached to the tip of the catheter 330 and what it sees is displayed in a catheter view 303. A heart icon 332 is displayed to identify the heart orientation.

Referring to FIG. 4, a context menu 402 containing registration actions is provided in the registration view 301. The inputs of the registration algorithm are EA points and a segmented surface that is represented by a dense triangle mesh, typically of 20-50 thousand triangles. The output is a rigid transformation matrix that describes the spatial relationship between the EA points and the segmented surface, where the reference coordinate system is of EA points. The rigid transformation matrix contains a 3×3 rotation matrix and a 3D translation vector.

In accordance with the present invention different types of registration may be performed. Examples of registration types include, but are not limited to, visual alignment registration, landmark registration, surface registration and local catheter registration. Visual alignment registration uses only one EA point. A user specifies a landmark point on the segmented surface that corresponds to the EA point. The registration is performed when the user selects the visual alignment link in the context menu 402. When visual alignment is selected and the EA point specified, a translation vector is solved based on the displacement between the landmark point and the EA point. The rotation matrix can be estimated either using the patient orientation vectors in the DICOM (Digital Imaging and Communications in Medicine) header or through the user interaction that rotates the LA surface to a similar orientation to the EA points.

Landmark registration uses three or more EA points. A user specifies three or more landmark points on the segmented surface that corresponds to three EA points. A unique rigid transformation minimizes the distances between the EA points and their corresponding landmark points. In accordance with the present invention, the landmark points should be picked so that they are far away from each other and not along a 3D line. Landmark registration is performed when the user selects the landmark registration link in the context menu 402. Corresponding landmark points 404, 406 (i.e., float and anchor points) are identified. The coordinates of the landmark points are also shown in the list 408 in the dialog bar.

Surface-based registration uses all of the EA points. After a new EA point is acquired, the registration is performed when the user selects the surface registration link in the context menu 402. Surface registration is automatic and iterative. At each iteration, the nearest corresponding point of each EA point is found on the segmented surface. A transformation, which minimizes the mean square error (MSE) of the correspondences, is computed. The iterations continue until the average point-to-point distance error is smaller than a predetermined threshold or the difference of this error between two consecutive iterations is smaller than a predetermined threshold.

The registration process is automatic since there is no need for a user to specify corresponding points. However, there may be many solutions to this minimization problem because of the local minima of the MSE. A good initialization of the transformation is required before surface-based registration is applied. In accordance with one embodiment of the present invention, visual alignment or landmark registration are performed prior to the surface-based registration to initialize the surface-based registration. When parts of the float surfaces are labeled by different weights, local anatomy registration will be performed.

Local surface-based registration uses one or more specific EA points which are given a higher weight for a better local registration. By default, all EA points have the same weight and local registration becomes a surface-based registration. The weight is controlled by a drop down menu 410 on the dialog bar. Local registration provides higher accuracy near those specific EA points. However, the overall accuracy is no longer optimal. The registration is performed when the user selects the local registration link in the context menu 402.

Figure 5A:
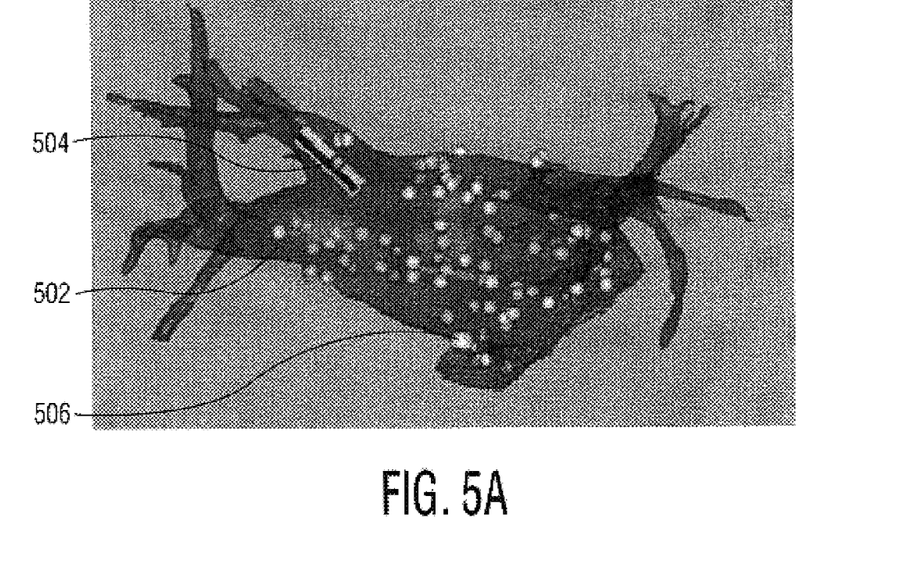
FIGS. 5a and 5b are visualizations of an image integration in accordance with the present invention.
Figure 5B:
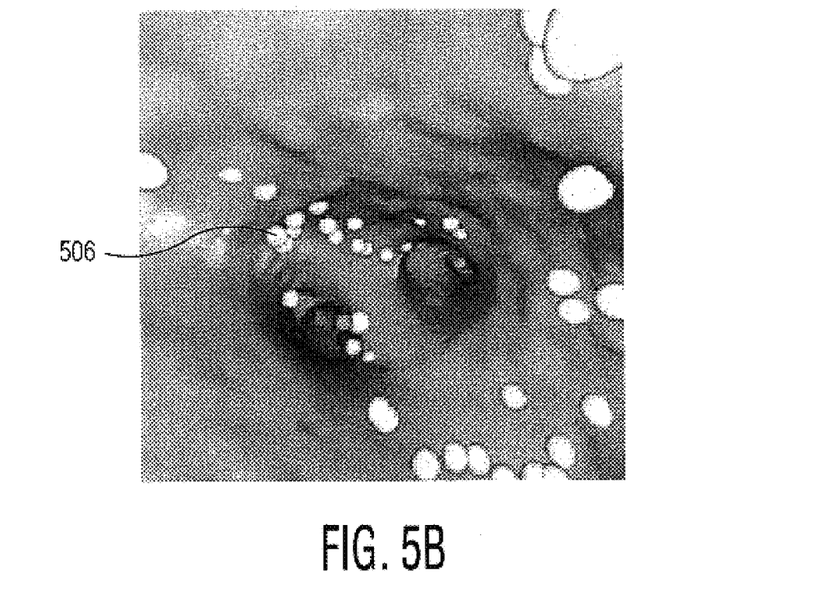

FIGS. 5a and 5b illustrate an example of an image integration of a pre-operative CT image of a LA 502 with a EA mapping of the LA in accordance with the present invention. Rendering both EA points and a segmented surface together provides the integrated view where the position of a catheter 504 is displayed in real time inside the segmented heart chamber as shown in FIG. 5a. By attaching a perspective camera (not shown) to the tip of the catheter 504, an endoscopic view can be shown that displays the interior wall of the heart chamber as shown in FIG. 5b. The white spheres 506 are the EA points.

The present invention finds the rigid transformation from the anatomical surface to the EA mapping data. Both anatomical surface and EA mapping data are 3D geometric objects but in different coordinate systems. Coordinates of EA points are relative to the EP system. Anatomical surface is represented by a triangle mesh that is extracted from a series of DICOM images. The triangle mesh comprises a list of vertices and a list of triangles. The vertex coordinates of the triangle mesh depend on the implementation of surface extraction. The surface may have been transformed according to the patient position and patient orientation. In order to provide an integrated view of anatomical surface and EA mapping data, the transformation matrix between two coordinate systems needs to be computed.

In accordance with the present invention, a number of corresponding 3D point pairs are identified. The transformation computation is based on finding a closed form solution to the least square fitting of these 3D point pairs. If there are two 3D points sets $\{p_i\}$ and $\{p'_i\}$, i=1, 2, ... N (here, $p_i$ and $p'_i$ are considered as 3×1 column vectors), and $$p'_i = Rp_i + T + n_i \quad (1)$$

where R is a 3×3 rotation matrix, T is a 3×1 translation vector, and $n_i$ is a 3×1 noise vector. A least squares problem is set up to determine R and T. The function to be minimized is $$E = \sum_{i=1}^{N} w_i \| p'_i - (Rp_i + T) \|^2 \quad (2)$$

where the coefficient $w_i$ is the weight for each correspondence.

In accordance with one embodiment of the present invention, the least squares fitting of two 3D point sets are performed as follows. First $\bar{p}$ and $\bar{p'}$ are defined to be the centroid of $\{p_i\}$ and $\{p'_i\}$, which are computed as $$\bar{p} = \frac{1}{N}\sum_{i=1}^{N} p_i \text{ and } \bar{p'} = \frac{1}{N}\sum_{i=1}^{N} p'_i \quad (3)$$

Let $q_i = p_i - \bar{p}$ and $q'_i = p'_i - \bar{p'}$. Next a 3×3 matrix H is calculated as follows:

$$H = \sum_{i=1}^{N} w_i q_i (q'_i)^t \quad (4)$$

where the superscript t denotes matrix transposition. The singular value decomposition (SVD) of H is $$H = UDV^t \quad (5)$$

where U and V are 3×3 orthonormal matrices and D is a diagonal matrix. The rotation matrix R is calculated as $$R = VU^t \quad (6)$$

For surface registration, the correspondence $p_i$ is found automatically by searching the closest point top $p'_i$ on the anatomical surface. After solving the transformation using the previous algorithm, the new correspondences are found based on the new transformation and used to update the transformation again. The surface registration is an iterative procedure, named iterative closest point (ICP) algorithm.

In accordance with ICP, the following loop is executed until a pre-specified condition is satisfied. First the nearest corresponding points $\{p_i\}$ and $\{p'_i\}$ are found. Next the transformation is computed based on the correspondence. Then the new transformation is applied to $\{p'_i\}$ and the steps are repeated. An example of a pre-specified condition is the average registration error. ICP can be used to determine with the registration error is below a threshold or maximal number of iterations have been reached. There may be many solutions to the registration problem because of the local minima of the function to be minimized. A good initialization of the transformation is required before surface registration is applied.

Having described embodiments for a system and method for automatically registering pre-operative high-resolution three dimensional (3D) cardiac images with corresponding intra-operative electrophysiological (EP) points of 3D electro-anatomical (EA) maps, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

We claim:

1. A computer-implemented method for automatically registering during an operative procedure a three dimensional (3D) pre-operative image of a heart with intra-operative electrophysiological (EP) points of a 3D electro-anatomical (EA) image map of the heart, the method performed by the computer comprising the steps of:

providing a segmented triangulated surface of the heart extracted from the pre-operative 3D image of the heart;

acquiring one or more EP points of the heart during an operative procedure;

selecting at least one EP point associated with a first cardiac chamber, and a first corresponding point on a surface of said first cardiac chamber from said segmented triangulated surface;

using said first corresponding points to register during said operative procedure the segmented triangulated surface of said first cardiac chamber with the EP points associated with said first cardiac chamber;

selecting at least one or more EP points associated with a second cardiac chamber, and second corresponding points on a surface of said second cardiac chamber from said segmented triangulated surface; and using said second corresponding points to register during said operative procedure the segmented triangulated surface of said second cardiac chamber with the EP points associated with said second cardiac chamber, wherein the registration of said segmented triangulated surface of said first cardiac chamber with the EP points associated with said first cardiac chamber are used to initialize the registration of the segmented triangulated surface of said second cardiac chamber with the EP points associated with said second cardiac chamber, and wherein the registration of said segmented triangulated surface of said first and second cardiac chambers with EP points associated with said first and second cardiac chambers is represented by a rigid transformation matrix.

2. The method of claim 1 wherein registering the segmented triangulated surface with the EP points further comprises the steps of:

specifying a landmark point on the segmented triangulated surface that corresponds to an EP point;

solving a translation vector based on displacement between the landmark point and the EP point.

3. The method of claim 1 wherein registering the segmented triangulated surface with the EP points further comprises the steps of:

specifying at least three landmark points on the segmented triangulated surface that correspond to at least three EP points; and performing a rigid transformation to minimize distances between the EP points and the corresponding landmark points.

4. The method of claim 3 wherein the at least three landmark points are not collinear.

5. The method of claim 1 wherein registering the segmented triangulated surface with the EP points comprises the steps of:

using an iterative process to identify a nearest corresponding point of each EP point to a landmark point on the segmented triangulated surface;

computing a transformation that minimizes a mean square error of the correspondence; and continuing the iterations until an average point-to-point distance error is smaller than a predetermined threshold.

6. The method of claim 1 wherein registering the segmented triangulated surface with the EP points further comprises the steps of:

assigning one or more specific EP points a higher weight;

specifying landmark points on the segmented triangulated surface that correspond to the one or more specific EP points; and performing a transformation to minimize distances between the specified EP points and the corresponding landmark points.

7. The method of claim 1, further comprising tracking movement of a catheter placed in the heart.

8. A system for automatically registering during an operative procedure a three dimensional (3D) pre-operative image of a heart with intra-operative electrophysiological (EP) points of a 3D electro-anatomical (EA) image map of the heart, the system comprising:

a display for displaying the pre-operative images in a first supporting view and the intra-operative EA image maps in a second supporting view;

a processor for maintaining the pre-operative images and intra-operative EA maps of the anatomical structure, the processor performing the following steps, providing a segmented triangulated surface of the heart extracted from the pre-operative 3D image of the heart;

acquiring one or more EP points of the heart during an operative procedure;

selecting at least one EP point associated with a first cardiac chamber, and a first corresponding point on a surface of said first cardiac chamber from said segmented triangulated surface;

using said first corresponding points to register during said operative procedure the segmented triangulated surface of said first cardiac chamber with the EP points associated with said first cardiac chamber;

using said registration of the segmented triangulated surface of said first cardiac chamber with the EP points associated with said first cardiac chamber to guide a transition from displaying said first cardiac chamber to displaying a second cardiac chamber;

selecting at least one or more EP points associated with a second cardiac chamber, and second corresponding points on a surface of said second cardiac chamber from said segmented triangulated surface; and using said second corresponding points to register during said operative procedure the segmented triangulated surface of said second cardiac chamber with the EP points associated with said second cardiac chamber, wherein the registration of said segmented triangulated surface of said first and second cardiac chambers with EP points associated with said first and second cardiac chambers is represented by a rigid transformation matrix.

9. The system of claim 8 wherein registering the segmented triangulated surface with the EP points further comprises the steps of:

specifying a landmark point on the segmented triangulated surface that corresponds to an EP point;

solving a translation vector based on displacement between the landmark point and the EP point.

10. The system of claim 8 wherein registering the segmented triangulated surface with the EP points further comprises the steps of:

specifying at least three landmark points on the segmented triangulated surface that correspond to at least three EP points; and performing a rigid transformation to minimize distances between the EP points and the corresponding landmark points.

11. The system of claim 10 wherein the at least three landmark points are not collinear.

12. The system of claim 8 wherein registering the segmented triangulated surface with the EP points comprises the steps of:

using an iterative process to identify a nearest corresponding point of each EP point to a landmark point on the segmented triangulated surface;

computing a transformation that minimizes a mean square error of the correspondence; and continuing the iterations until an average point-to-point distance error is smaller than a predetermined threshold.

13. The system of claim 8 wherein registering the segmented triangulated surface with the EP points further comprises the steps of:

assigning one or more specific EP points a higher weight;

specifying landmark points on the segmented triangulated surface that correspond to the one or more specific EP points; and performing a transformation to minimize distances between the specified EP points and the corresponding landmark points.

14. The system of claim 8 further comprising a catheter placed in the heart wherein said processor tracks movement of the catheter in the heart.

15. The method of claim 1, wherein the second cardiac chamber is the same as the first cardiac chamber.

16. The system of claim 8, wherein the second cardiac chamber is the same as the first cardiac chamber.

17. The method of claim 1, wherein the method performed by the computer further comprises aligning the orientation of the segmented triangulated surface to an anterior posterior view.

18. The system of claim 8, wherein the method performed by the processor further comprises aligning the orientation of the segmented triangulated surface to an anterior posterior view.

* * * * *